(12) United States Patent
Winston et al.

(10) Patent No.: US 7,288,087 B2
(45) Date of Patent: *Oct. 30, 2007

(54) EXPANDABLE LASER CATHETER

(75) Inventors: Thomas R. Winston, Leawood, KS (US); John M. Neet, Lawrence, KS (US)

(73) Assignee: Intraluminal Therapeutics, Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/270,917

(22) Filed: Oct. 15, 2002

(65) Prior Publication Data

US 2003/0109859 A1    Jun. 12, 2003

Related U.S. Application Data

(60) Continuation of application No. 09/564,137, filed on May 3, 2000, now Pat. No. 6,485,485, which is a division of application No. 09/133,575, filed on Aug. 13, 1998, now Pat. No. 6,106,515.

(51) Int. Cl.
*A61B 18/18* (2006.01)

(52) U.S. Cl. .......................... 606/15; 606/7
(58) Field of Classification Search ............ 606/7, 606/8, 14–17
See application file for complete search history.

(56) References Cited

U.S. PATENT DOCUMENTS 4,790,310 A * 12/1988 Ginsburg et al. .............. 606/7
4,854,315 A *  8/1989 Stack et al. .................... 606/3
5,203,779 A *  4/1993 Muller et al. .................. 606/7
5,290,278 A *  3/1994 Anderson ..................... 606/15
5,298,026 A *  3/1994 Chang ......................... 606/15
5,449,354 A *  9/1995 Konwitz et al. ............. 606/15
5,478,339 A * 12/1995 Tadir et al. .................. 606/15
6,106,515 A *  8/2000 Winston et al. ............. 606/15
6,485,485 B1* 11/2002 Winston et al. ............. 606/15

* cited by examiner

*Primary Examiner*—Michael Peffley
(74) *Attorney, Agent, or Firm*—Armstrong Teasdale LLP (57) ABSTRACT

Expandable laser catheters for utilizing laser energy to remove obstructions from body passages are described. In one embodiment, the laser catheter includes a shaftway having a distal end including a flexible portion configured in a series of radial folds. Multiple optical fibers, configured to transmit laser energy, extend along the shaftway and are attached to the flexible portion. An inflatable, ring-shaped balloon is attached to the catheter within the flexible portion. In use, the catheter is inserted into a body passage such as an artery, and advanced until the distal end is adjacent to an obstruction. The balloon is inflated to expand the flexible portion and to bring the optical fibers nearer the inner wall of the body passage. Laser energy is directed by the optical fibers toward targeted regions of the obstruction. As the catheter is advanced and the process repeated, a core is formed from the obstruction and contained within the flexible portion. The flexible portion is then contracted to hold the core, and the core is removed from the body passage by withdrawing the catheter.

22 Claims, 5 Drawing Sheets

EXPANDABLE LASER CATHETER

This application is a continuation of U.S. patent application Ser. No. 09/564,137, filed May 3, 2000, now U.S. Pat. No. 6,485,485, which is a divisional of U.S. patent application Ser. No. 09/133,575, filed Aug. 13, 1998, now U.S. Pat. No. 6,106,515. This application claims priority from U.S. patent application Ser. No. 09/564,137, filed May 3, 2000, now U.S. Pat. No. 6,485,485, which is a divisional of U.S. patent application Ser. No. 09/133,575, filed Aug. 13, 1998, now U.S. Pat. No. 6,106,515, both of which are hereby incorporated by reference.

FIELD OF THE INVENTION

This invention relates generally to laser catheters and more particularly, to an expandable laser catheter for removing obstructions from body passages.

BACKGROUND OF THE INVENTION

Atherosclerotic plaque is known to build up on the walls of arteries in the human body. Such plaque build-up restricts circulation and often causes cardiovascular problems, especially when the build-up occurs in coronary arteries. Other body passages such as the esophagus, ureter and bile ducts, for example, are subject to blockage by tumorous tissue. Accordingly, it is desirable to remove or otherwise reduce plaque build-up and other tissue obstructions from such body passages.

Known catheters use laser energy to remove plaque build-up on artery walls. One such known catheter has a laser source and a catheter body. The catheter body has a proximal end and a distal end, or head, and multiple optical fibers extending between the proximal and distal ends. The laser source is coupled to the optical fibers at the proximal end of the catheter body and is configured to transmit laser energy through the optical fibers.

To remove an obstruction from a body passage, such as atherosclerotic plaque in an artery, the catheter is positioned in the artery so that the distal end of the catheter is adjacent to the plaque. The laser source is then energized so that laser energy travels through the optical fibers and photoablates the plaque adjacent the distal end of the catheter. The catheter is then advanced further through the artery to photoablate the next region of plaque build-up.

While known laser catheters are generally acceptable for removing small obstructions, such catheters are limited to opening a path the size of the catheter head on each pass through the body passage. The multiple passes which are required for removing larger areas of obstruction increase the possibility of damaging the passage inner wall. In addition, multiple passes increase the possibility that a piece of the obstruction will break free, enter the blood stream and result in vessel blockage. Other known laser catheters are limited by the relative inflexibility of the catheter distal end which may inflict damage to body passage inner walls as the catheter is advanced.

Accordingly it would be desirable to provide a laser catheter which can remove substantial portions of an obstruction in a single pass. It would also be desirable to provide a laser catheter having a flexible, adjustable distal end which can substantially conform to the inner dimensions of the body passageway to minimize damage to the inner wall. It would be further desirable to provide a laser catheter which can expand and contract during photoablation to increase the area of obstruction which may be photoablated in a single pass through a body passage.

SUMMARY OF THE INVENTION

These and other objects may be attained by a laser catheter which, in one embodiment, includes a shaftway having a proximal end and a distal end including a flexible portion. The flexible portion is fabricated from a pliable material and is configured in folds which are radially oriented about the longitudinal axis of the catheter. The flexible portion is configured to be expanded by, for example, an inflatable balloon which is attached within the flexible portion. Optical fibers extend along the length of the catheter to transmit laser energy from the proximal end to the distal end of the catheter, and are attached to the catheter at the distal end. The ends of the optical fibers, at their attachments to the distal end, are directed toward targeted regions of an obstruction.

In use, a guidewire is inserted into a body passage such as an artery and advanced past the obstruction. The catheter is then advanced over the guidewire through the artery until the distal end of the catheter is adjacent to the obstruction, such as atherosclerotic plaque. The balloon is then inflated to expand the flexible portion of the distal end. Upon expansion, the flexible portion substantially conforms to the inner dimensions of the body passage and is enlarged so that the flexible portion can hold a core of material from the obstruction. A laser connected to the optical fibers at the catheter proximal end is then energized, and the laser energy transmitted through the optical fibers photoablates the obstruction in the regions targeted by the optical fibers. The catheter is then advanced and the process repeated.

As the catheter is advanced and targeted regions photoablated, the catheter detaches a separate core of material from the obstruction. As the core is formed the catheter advances over the core so that ultimately the core is completely contained within the flexible portion. To remove the core of the obstruction, the balloon is deflated and the flexible portion contracts and holds the core of the obstruction. The catheter is then withdrawn from the body passage to remove the core of the obstruction from the body passage.

In an alternative embodiment, the laser catheter utilizes mechanical spring force to expand the distal end of the laser catheter. In this alternative embodiment, the optical fibers are attached to a stiff shaftway. A fin structure including a plurality of fins fabricated from a spring material is attached to the distal end of the shaftway. The stiff shaftway is capable of transmitting torque to the distal end so that the fin structure can be rotated, thus facilitating advancement of the fin structure, and complete removal of the obstruction. The fins have a substantially rolled shape and are expandable from a retracted position to an extended position. In both the retracted position and the extended position the fins retain a substantially rolled shape which substantially conforms to the inner dimensions of the body passage, to minimize damage to the inner wall of the body passage. At the fin structure the ends of the optical fibers are attached and spread across the fins and are directed parallel to the shaftway. The laser catheter further includes an outer catheter body or sheath slidably disposed over the shaftway to retain the fin structure in the retracted position.

In use of the alternative embodiment, a guide wire is introduced into a body passage and advanced past the obstruction. The laser catheter is introduced over the guide wire and advanced toward the obstruction. When the distal end of the catheter is adjacent the obstruction, the shaftway is rotated and advanced so that the fin structure is pushed out of the outer catheter body, thus releasing the fins from the retracted position and allowing them to expand to the extended position. In the extended position, the fins contact the passage inner wail and the ends of the optical fibers are directed parallel to the inner wall of the passage. The fin structure can be further advanced along the passage wall by advancing the shaftway and sliding the fin structure along the passage wall. Laser energy is used to photoablate regions of the obstruction targeted by the optical fibers. The mounting of the optical fibers on the fin structure allows the obstruction to be removed from around the passage central axis (around the guide wire) to the outside diameter of the passage, with the fins protecting normal passage inner wall from photoablation. When the obstruction has been removed, the fin structure is rotated and pulled back into the outer catheter body, thus causing the fins to retract to the retracted position. The catheter is then removed from the body passage.

In additional alternative embodiments especially useful for opening in-stent restenosis, laser energy may be directed radially outward from the shaftway instead of parallel to the shaftway. This may be accomplished by attaching the ends of the optical fibers at the fin structure so that the ends of the fibers are directed radially outward from the shaftway, or alternatively, by coupling prisms to the ends of the optical fibers at the fin structure to direct laser energy radially outwards from the shaftway.

The above described laser catheter removes substantial portions of an obstruction in a single pass by expanding the distal end of the catheter to substantially conform to the inner dimensions of the body passage. The laser catheter further minimizes damage to the body passage inner wall with a flexible, adjustable distal end. Further, the laser catheter may be expanded and contracted during photoablation to increase the area of obstruction which may be photoablated in a single pass. By removing substantial portions of an obstruction in a single pass, the laser catheter obviates the need for multiple and potentially damaging passes through the body passage.

DETAILED DESCRIPTION

Figure 1:
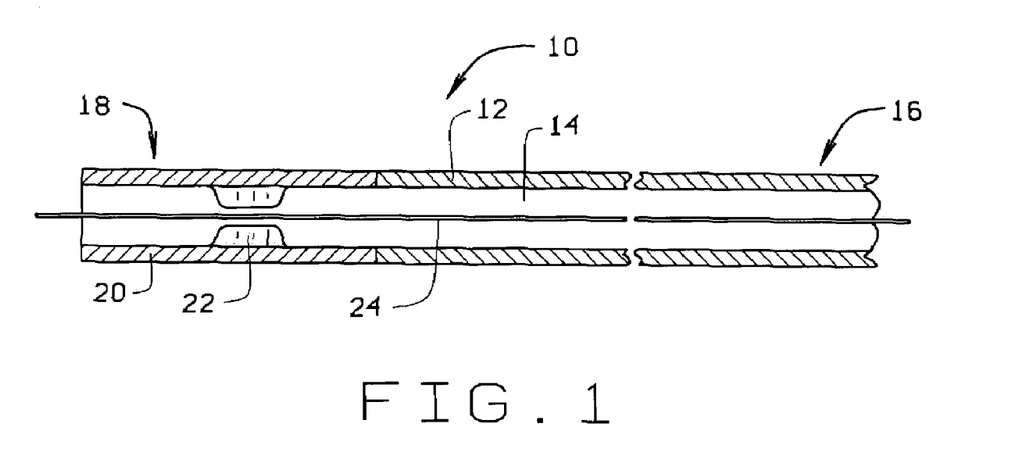
FIG. 1 is a sectional view of a laser catheter.

FIG. 1 is a sectional view of a laser catheter 10 in accordance with one embodiment of the present invention. Catheter 10 includes a shaftway 12 which defines a lumen 14 about a longitudinal axis, and has a proximal end 16, a distal end 18, and a flexible portion 20 adjacent distal end 18. Flexible portion 20 is configured in a plurality of folds having a radial orientation about the longitudinal axis of lumen 14. A ring-shaped inflatable balloon 22, or other means for expanding flexible portion 20, is attached to shaftway 12 within flexible portion 20. Balloon 20 may instead be attached to the guide wire or a mechanical device. Catheter 10 extends over a conventional guidewire 24. Balloon 22 is positioned from about 1 mm to about 10 mm behind the end of flexible portion 20. Balloon 22 communicates via air lines or tubing (not shown) as known in the art to a means for inflating the balloon, such as a syringe, air compressor or other air pressure providing device (not shown). Multiple optical fibers (not shown in FIG. 1) extend longitudinally along the length of catheter 10.

In one embodiment, shaftway 12 is approximately 80 to 150 cm long and is fabricated from conventional catheter materials such as, for example, polyurethane. Lumen 14 has a diameter of approximately 1 to 5 mm, and the outer diameter of shaftway 12 is approximately 1.5 to 6 mm. Flexible portion 20 is approximately 2 to 5 cm long and is fabricated from a pliable material such as, for example, polyurethane. In the folded configuration, the outer diameter of flexible portion 20 is approximately the same size as the outer diameter of shaftway 12. In one embodiment, flexible portion 20 is bonded to shaftway 12 by thermal fusion or an adhesive.

Figure 2:
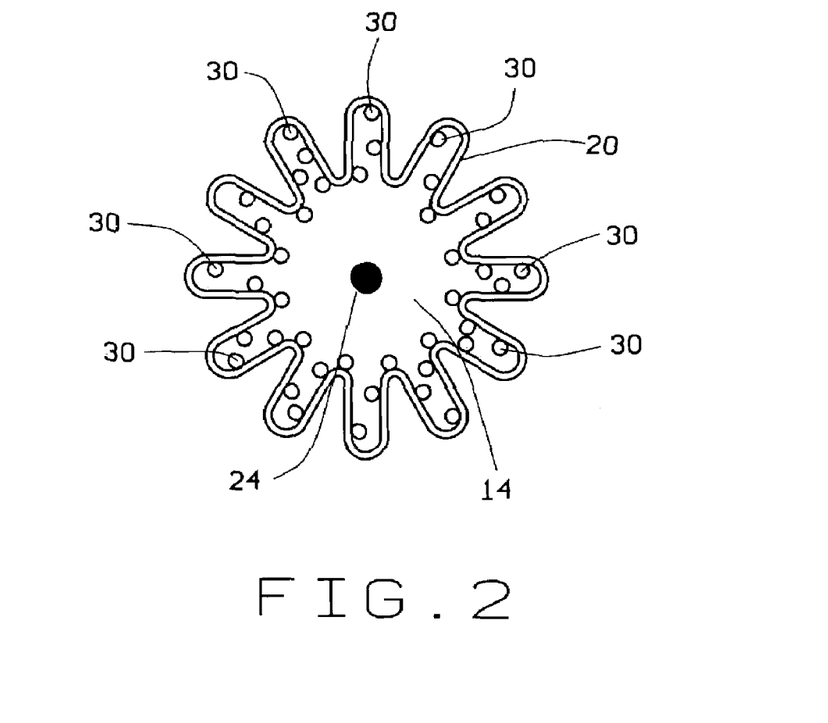
FIG. 2 is a cross-sectional view of a distal end of the laser catheter.

Referring to FIG. 2, catheter 10 includes multiple optical fibers 30. Fibers 30 extend longitudinally along the length of shaftway 12 into flexible portion 20, and are attached to flexible portion 20. Fibers 30 are of a type known in the art of laser catheters and are configured to transmit laser energy. In one embodiment, optical fibers 30 extend through lumen 14 and are embedded in the pliable material forming flexible portion 20. Optical fibers 30 have proximal ends (not shown) which are configured to connect through an optical fiber port (not shown) to a laser connector and a laser (not shown), such as an excimer laser, Nd:YAG, holmium or $CO_2$ laser. In one embodiment, the laser is configured to produce laser energy of a wavelength of about 0.3 microns to about 2.0 microns. The composition of optical fibers 30 depends upon the chosen laser and the wavelength of laser energy that the laser produces. In one embodiment, the laser is an excimer laser producing energy of a wavelength of about 0.3 microns, requiring optical fibers made of quartz.

Figure 3:
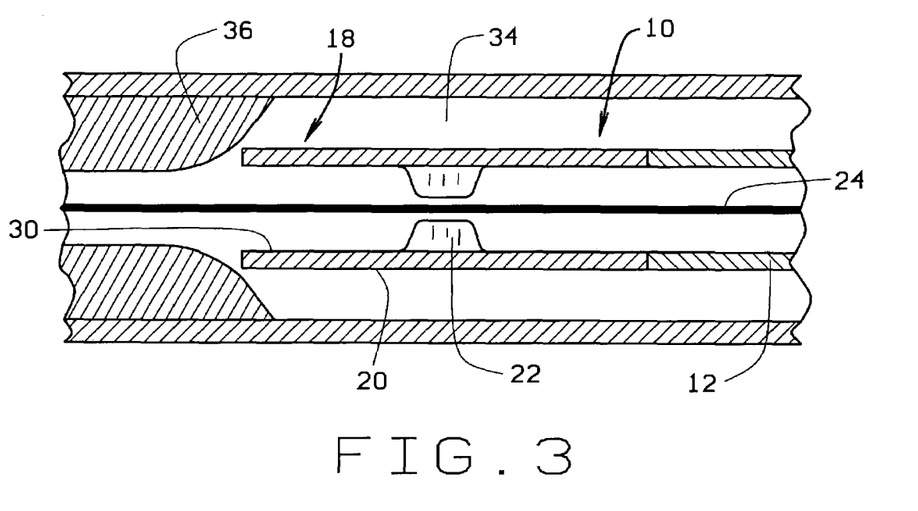
FIG. 3 is a sectional view of the distal end of the laser catheter positioned adjacent to an obstruction in a body passage.

FIG. 3 is a sectional view of catheter 10 in use within a body passage 34. In use, guidewire 24 is inserted into body passage 34 and advanced past an obstruction 36. Catheter 10 is then inserted into body passage 34 over guidewire 24 and advanced until distal end 18 is adjacent obstruction 36. Specifically, catheter 10 is advanced until distal end 18 is positioned to contact obstruction 32 or to be within about 2 mm of obstruction 32. The relative distance of distal end 18 to obstruction 36 is determined using radiopaque markers and fluoroscopy, or other imaging techniques known in the art. After flexible portion 20 is correctly positioned adjacent obstruction 36, balloon 22 is inflated by applying air pressure through tubing connecting balloon 22 with, for example, a syringe. Expansion of balloon 22 causes the flexible portion 20 to expand in the radial dimension as the folds are unfolded creating a core retention portion 38 within flexible portion 20. Balloon 22 is expanded until flexible portion 20 is adjacent to the inner wall of body passage 34, as determined in one embodiment by a fluoroscopy image. The laser is energized so that laser energy travels through fibers 30 to photoablate regions of obstruction 36.

Figure 4:
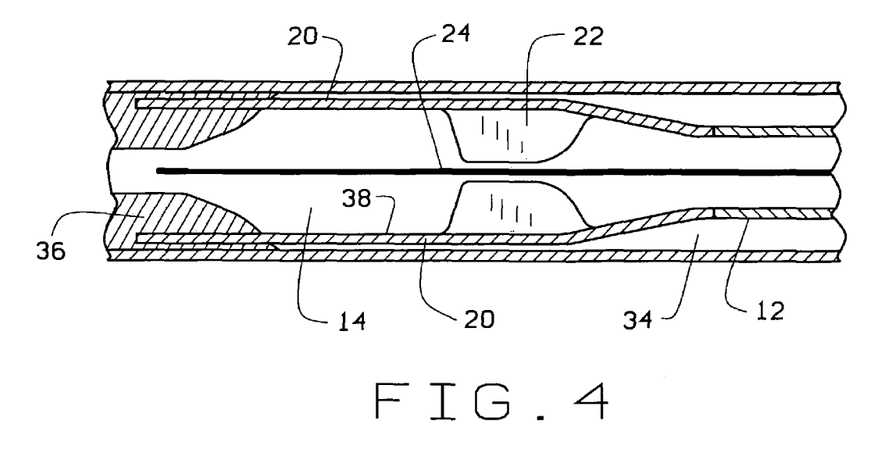
FIG. 4 is a sectional view of the catheter distal end within a body passage after expansion of the flexible portion and partial photoablation of the obstruction.
Figure 5:
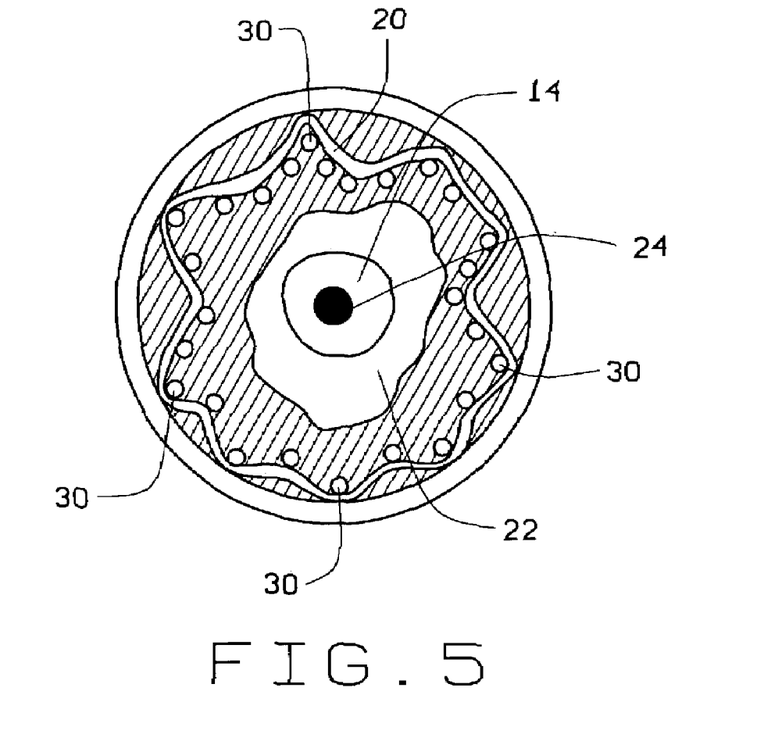
FIG. 5 is a cross-sectional view of the catheter distal end within a body passage after expansion of the flexible portion and partial photoablation of the obstruction.

Referring to FIGS. 4 and 5, flexible portion 20 is then advanced further through obstruction 36 and the process is repeated. Specifically as shown in FIG. 5, the end faces of optical fibers 30 in expanded flexible portion 20 are positioned to direct laser energy toward regions of obstruction 32 which approach or meet the inner wall of passage 30.

Figure 6:
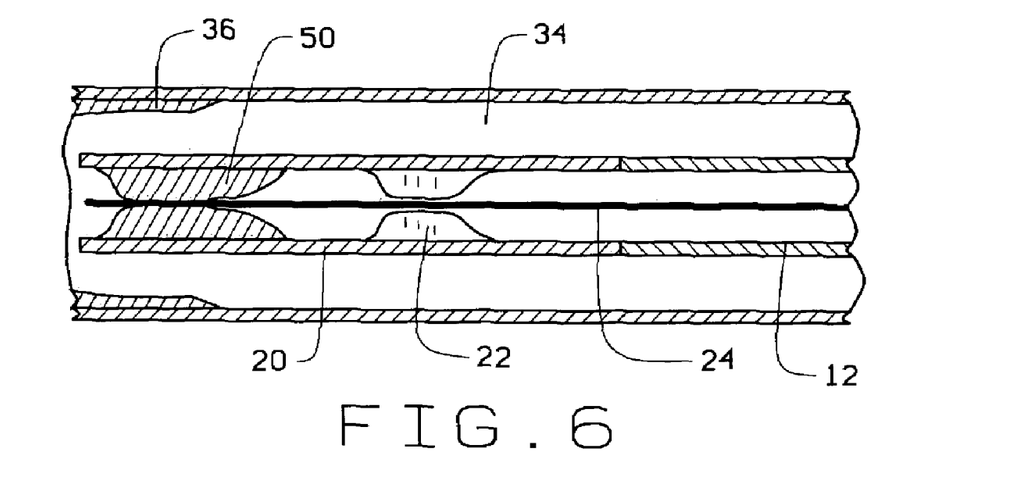
FIG. 6 is a sectional view of the catheter distal end after formation of a core of obstruction and contraction of the flexible portion.
Figure 7:
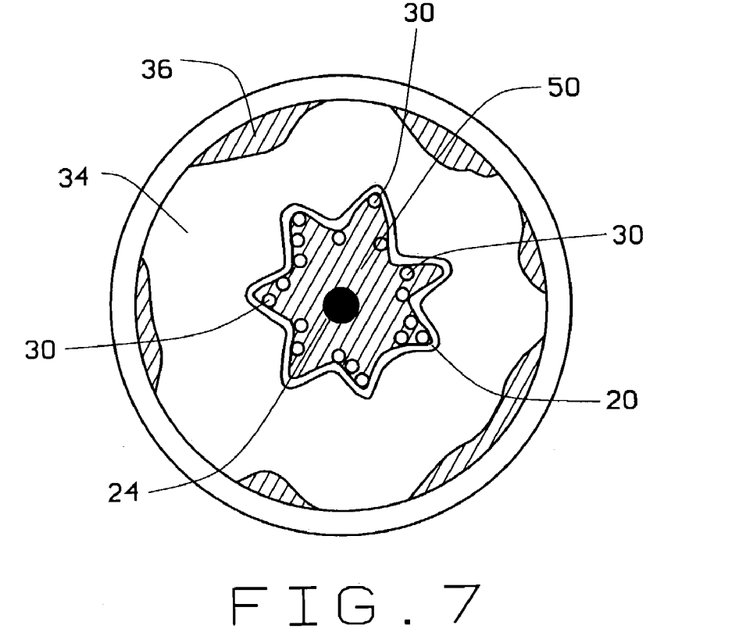
FIG. 7 is a cross-sectional view of the catheter distal end after formation of the core of obstruction and contraction of the flexible portion.

Referring to FIG. 6, catheter 10 photoablates regions of obstruction 36. Catheter 10 is then advanced further along passage 30. A core 50 of material from obstruction 36 is formed as catheter 10 photoablates regions of obstruction 36 and is advanced. If catheter 10 is advanced through entire obstruction 36, or if the entire length of flexible portion 20 is advanced through obstruction 36, air pressure is removed from balloon 22. As a result, flexible portion 20 contracts and retains core 50 within core retention portion 38. More particularly, as balloon 22 is deflated and flexible portion 20 contracts, core 50 is retained within the folds of flexible portion 20. Core 50 is then removed from body passage 34 by withdrawing catheter 10 from body passage 34. FIG. 7 is a cross-sectional view of contracted flexible portion 20 within body passage 34, retaining core 50 after core 50 has been formed.

In an alternative embodiment of the method, obstruction 36 is entirely or substantially removed from body passage 34 by photoablation. Balloon 22 is expanded and contracted to impart radial motion to fibers 30 during photoablation, thereby increasing the area of obstruction 36 which is exposed to laser energy on a single pass through body passage 34. In addition, shaftway 12 may be rotated to impart tangential motion to fibers 30 to further facilitate substantial photoablation of obstruction 36.

In another alternative embodiment of catheter 10, shaftway 12 may be slidably inserted through an outer catheter body (not shown) to provide rigidity to flexible portion 20 as flexible portion 20 is advanced through body passage 34. Catheter 10 is advanced through body passage 34 until flexible portion 20 is within a defined distance of obstruction 36 as defined above. Flexible portion 20 is then extended out of the outer catheter body and is free to expand. Alternatively, the outer catheter body may be partially retracted to free flexible portion 20. After expansion of flexible portion 20, photoablation and formation of core 50, flexible portion 20 retaining core 50 is retracted within the outer catheter body and catheter 10 is withdrawn from body passage 34.

Figure 8:
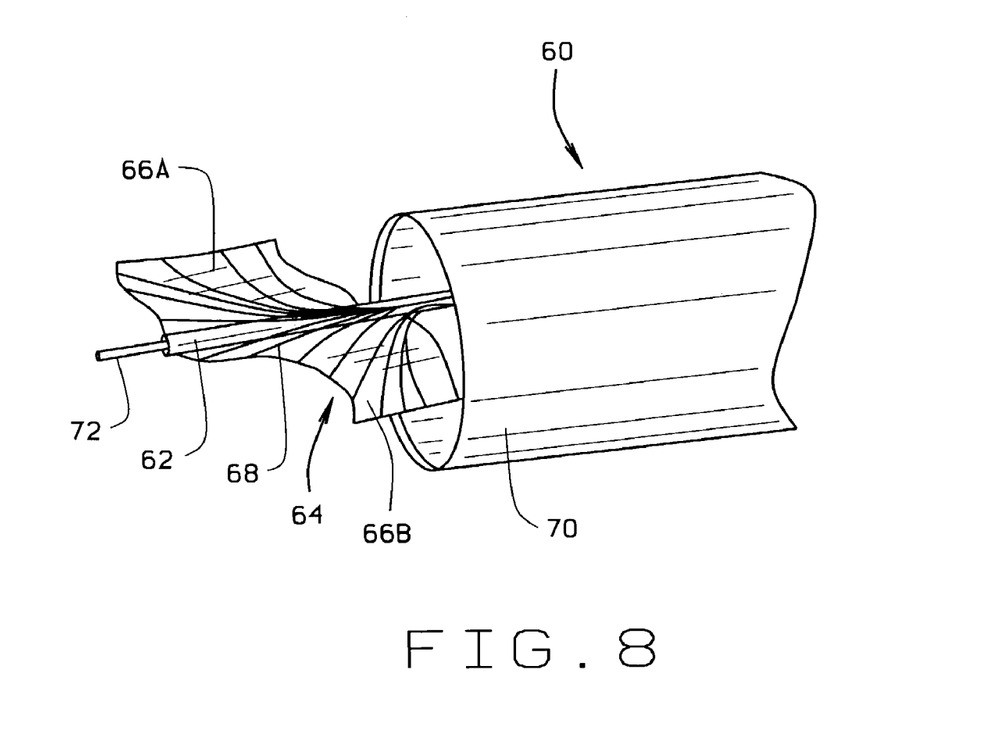
FIG. 8 is a perspective view of a distal end of a laser catheter.

In an alternate embodiment shown in FIG. 8, catheter 60 utilizes mechanical spring force to expand the distal end of the laser catheter. Catheter 60 includes a stiff shaftway 62 having a proximal end (not shown) and a distal end 64. A fin structure including fins 66A and 66B is attached to distal end 64. Fins 66A and 66B extend from shaftway 62 and are configured to have a retracted position (not shown) and an extended position (shown in FIG. 8). Stiff shaftway 62 is capable of transmitting torque to the distal end and allows the fin structure to be rotated to facilitate advancement of the fin structure, and complete removal of the obstruction. Fins 66A and 66B have a substantially rolled shape in both the retracted position and the extended position, allowing fins 66A and 66B to substantially conform to the inner dimensions of the body passage, to minimize damage to the inner wall of the body passage. Optical fibers 68, similar to optical fibers 30, extend from the proximal end to distal end 64 and are attached and spread across fins 66A and 66B. Proximal ends of optical fibers 68 (not shown) may be configured to connect through an optical fiber port (not shown) to a laser connector and a laser (not shown), such as an excimer laser, Nd:YAG, holmium or $CO_2$ laser. Shaftway 62 is slidably positioned within an outer catheter body 70 which is configured to retain fins 66A and 66B in the retracted position. Shaftway 62 slidably extends over guidewire 72, which is similar to guidewire 24.

In one embodiment, shaftway 62 is fabricated from conventional catheter materials such as, for example, stainless steel hypodermic tubing. Fins 66A and 66B are fabricated from a spring material such as a metal alloy foil. In one embodiment, the foils generally have a thickness of about 0.00 1 inches and may be fabricated from, for example, stainless steel, nitinol or precipitation hardened steel. Thus, fins 66A and 66B expand from the retracted rolled shape to the extended rolled shape due to the mechanical spring force of the foil. Fins 66A and 66B are attached to shaftway 62 by welding or brazing, are about 10 to about 30 mm long, and extend about 1.5 mm to about 15 mm from their attachments at shaftway 62. Outer catheter body 70 is fabricated from conventional catheter materials as known in the art.

In one embodiment, distal end 64 includes two fins 66A and 66B, but any number of fins may be used. Distal ends of optical fibers 68 are attached to the spring material forming fins 66A and 66B so that the ends of optical fibers 68 are at an angle, or parallel, to the central axis of the body passage. For example, the distal ends of optical fibers 68 may be directed in any desired direction from parallel to the central axis of the body passage, to perpendicular to the inner wall of the body passage. The desired direction is determined by the size and shape of the obstruction to be excised. For example, it is particularly desirable to aim fiber ends at a substantial angle, including substantially perpendicularly, to the body passage inner wall for photoablation of well-defined regions of obstruction, such as restenosis within a stent.

Figure 9:
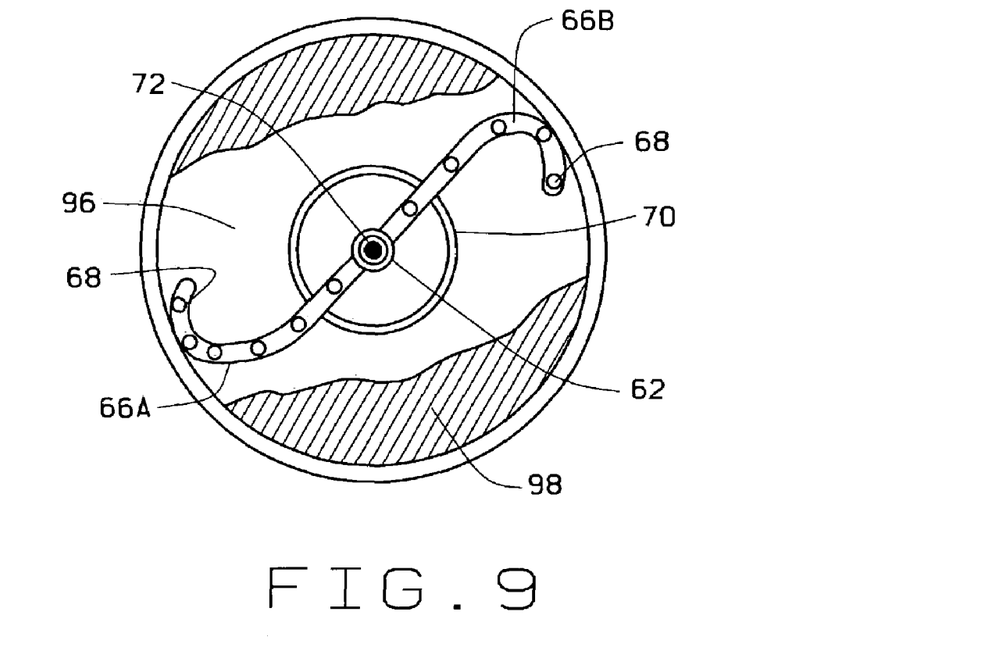
FIG. 9 is a cross-sectional view of the catheter distal end shown in FIG. 8 and positioned within a body passage.

FIG. 9 is a cross-sectional view of distal end 64 positioned within a body passage 96 and adjacent to an obstruction 98. Distal end 64 is shown extending beyond outer catheter body 70. Fins 66A and 66B are in the extended position.

Figure 10:
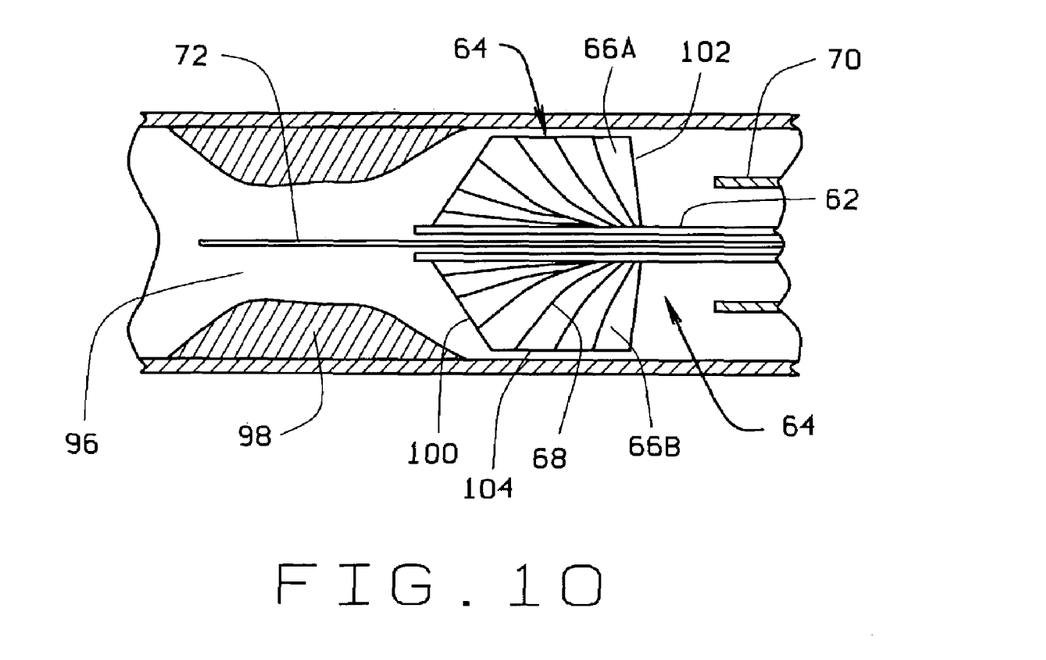
FIG. 10 is a sectional view of the catheter distal end shown in FIG. 8 and positioned within the body passage.

FIG. 10 is a sectional view of distal end 64 with fins 66A and 66B in the extended position as shown in FIG. 9. In one embodiment, fins 66A and 66B each have a leading edge 100, a trailing edge 102, and a peripheral edge 104. To facilitate navigation of distal end 64 through curves in body passage 96, fins 66A and 66B are tapered along leading edge 100 and trailing edge 102 so that fins 66A and 66B are widest at their attachments to shaftway 62 and shortest along peripheral edge 104.

In use, guidewire 72 is inserted into body passage 96 and advanced past obstruction 98. Catheter 60 is then inserted into body passage 96 over guidewire 72. Fins 66A and 66B are retained in the retracted position within outer catheter body 70. Catheter 60 is advanced within passage 96 until distal end 64 is positioned proximate obstruction 98, for example, within about 2 mm. Distal end 64 is extended out of outer catheter body 70 by advancing shaftway 62, thereby releasing the restraint on fins 66 and allowing fins 66 to extend and conform to the inner dimensions of body passage 96. The laser coupled to the proximate ends of optical fibers 68 is energized so that laser energy travels through fibers 68 to photoablate regions of obstruction 98. Distal end 64 may be rotated and advanced further along passage 96 for photoablation of any remaining regions of obstruction 98. The spring material forming fins 66A and 66B protects against damage to the passage inner wall by preventing direct contact by optical fibers 68 with the inner wall. Once obstruction 98 has been photoablated, distal end 64 is pulled back into outer catheter body 70 to retract fins 66A and 66B and facilitate removal from body passage 96.

Alternate embodiments of the laser catheters described herein may be used to remove small or large regions of atherosclerotic plaque from blocked blood vessels, or regions of tumor invading an esophagus, ureter, urethra, bile duct or other body passage. The catheters may also be used, for example, to aid in the removal of excess or abnormal cartilage in body joints such as knees, or in disc spaces between vertebral bodies. The catheters may be used without guidewires and instead with alternate guidance methods such as optical coherence tomography (OCT), ultrasound, CT scanning or fluoroscopy. The catheters may be surgically introduced to body passages or elsewhere in the body using known instruments such as arthroscopes, endoscopes, colonoscopes, bronchoscopes, laparoscopes, etc. The distal end faces of the optical fibers may be rounded, or square-cut, cut at an angle, or connected to an optical prism lens to more precisely target certain regions of the obstruction.

To further minimize damage to the body passage inner wall, the flexible portion substantially conforms to the inner dimensions of the body passage. In an alternate method of use, the flexible portion is expanded and contracted during photoablation to increase the area of obstruction which is removed by direct photoablation in one pass through the body passage.

The above described laser catheter improves the efficacy and safety of using laser energy to remove large areas of an obstruction from a body passage. The laser catheter of the present invention uses photoablation to create a core of an obstruction which is then removed as a single mass at one time. The laser catheter therefore minimizes damage to body passage walls by obviating the need for multiple passes through the body passage. Alternate embodiments of the method for using the laser catheter include expanding and contracting the flexible distal portion during photoablation of the obstruction, thereby photoablating large areas of obstructions in one pass and minimizing damage to body passage walls. In addition, the laser catheter includes a distal end which substantially conforms to the inner dimensions of the body passageway and further minimizes damage to body passage inner walls.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. Accordingly, the spirit and scope of the invention are to be limited only by the terms of the appended claims.

The invention claimed is:

1. A laser catheter for excising an obstruction from a body passage having an internal wall, said catheter comprising:
   a catheter body having a bore therethrough;
   an extendable structure including at least one extending member;
   a flexible shaftway having a proximal end, a distal end, and an outer surface, said extendable structure mechanically attached to said shaftway and extending therefrom, said shaftway configured to slidably extend through the bore of said catheter body; and
   a plurality of optical fibers, said fibers having proximal ends, distal ends, and distal end faces, the distal ends of said optical fibers attached to said extendable members and wherein when said extendable members are fully extended, flow through the body passage is only partially obstructed.

2. The laser catheter in accordance with claim 1 wherein said extendable members are fabricated from an expandable material.

3. The laser catheter in accordance with claim 1 wherein said expandable material comprises a metal alloy foil having a thickness of about 0.001 inches.

4. The laser catheter in accordance with claim 3 wherein said foil comprises a stainless steel.

5. The laser catheter in accordance with claim 3 wherein said foil comprises nitinol.

6. The laser catheter in accordance with claim 3 wherein said foil comprises a precipitation hardened steel.

7. The laser catheter in accordance with claim 1 further comprising a laser for providing laser energy, said laser connected to said proximal ends of said optical fibers.

8. The laser catheter in accordance with claim 1 wherein said laser comprises an excimer laser.

9. The laser catheter in accordance with claim 1 wherein the distal end faces of said optical fibers are configured to direct the laser energy at an acute angle to the internal wall of the body passage.

10. The laser catheter in accordance with claim 1 wherein the distal end faces of said optical fibers are configured to direct the laser energy in a direction substantially perpendicular to the internal wall of the body passage.

11. The laser catheter in accordance with claim 1 further comprising a guidewire, wherein said shaftway is configured to slidably extend over said guidewire.

12. The laser catheter in accordance with claim 1 wherein said extendable members have a substantially rolled shape in both an extended position and in a retracted position.

13. The laser catheter in accordance with claim 12 wherein said extendable members comprise a spring material, said extendable members configured to expand from the retracted position to the expanded position due to a mechanical spring force of said spring material.

14. The laser catheter in accordance with claim 1 wherein said flexible shaftway is configured to apply a torque to said extendable members to facilitate movement of said catheter.

15. The laser catheter in accordance with claim 1 wherein said extendable members are configured to extend when said distal end of said shaftway is extended out from the bore of said catheter body.

16. The laser catheter in accordance with claim 1 wherein said extendable members are configured to prevent said optical fibers from directly contacting the internal wall of the body passage.

17. A laser catheter according to claim 1 wherein said extendable members are fins.

18. A laser catheter comprising:
   a catheter body having a bore therethrough;
   an extendable structure including at least one extending member;
   a flexible shaftway having a proximal end, a distal end, and an outer surface, said extendable structure mechanically attached to said shaftway and extending therefrom, said shaftway configured to slidably extend through the bore of said catheter body; and
   a plurality of optical fibers, said fibers having proximal ends, distal ends, and distal end faces, the distal ends of said optical fibers attached to said extendable members and wherein when said extendable members are fully extended, flow through the body passage is only partially obstructed.

19. A laser catheter according to claim 18 wherein each said extendable member comprises a leading edge, at least a portion of said optical fiber distal ends flush with said leading edge.

20. A laser catheter according to claim 18 wherein each said extendable member comprises a peripheral edge opposite said shaftway, at least a portion of said optical fiber distal ends flush with said peripheral edge.

21. A laser catheter according to claim 20 wherein each said extendable member comprises a substantially rolled shape originating at said peripheral edge.

22. A laser catheter according to claim 18 wherein said extendable members are fins.

* * * * *